US010864038B2

(12) United States Patent
Motai

(10) Patent No.: US 10,864,038 B2
(45) Date of Patent: Dec. 15, 2020

(54) DIGESTIVE-TRACT TREATMENT METHOD

(71) Applicant: OLYMPUS CORPORATION, Tokyo (JP)

(72) Inventor: Kosuke Motai, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 227 days.

(21) Appl. No.: 16/025,089

(22) Filed: Jul. 2, 2018

(65) Prior Publication Data

US 2020/0000513 A1  Jan. 2, 2020

(51) Int. Cl.
*A61B 18/14* (2006.01)
*A61B 17/30* (2006.01)
*A61B 17/00* (2006.01)
*A61F 2/00* (2006.01)
*A61F 2/04* (2013.01)

(52) U.S. Cl.
CPC ...... *A61B 18/1445* (2013.01); *A61B 17/0057* (2013.01); *A61B 17/30* (2013.01); *A61B 2017/00818* (2013.01); *A61B 2017/306* (2013.01); *A61B 2018/144* (2013.01); *A61B 2018/1465* (2013.01); *A61F 2/0009* (2013.01); *A61F 2/04* (2013.01)

(58) Field of Classification Search
CPC . A61B 17/30; A61B 17/0401; A61B 17/0469; A61B 17/0057; A61B 2017/306; A61B 2017/00818; A61B 2017/0409
See application file for complete search history.

(56) References Cited

U.S. PATENT DOCUMENTS

2002/0010480 A1* 1/2002 Sancoff .............. A61B 17/0644
606/148
2011/0277778 A1 11/2011 Alexander et al.

FOREIGN PATENT DOCUMENTS

EP  2386270 A2  11/2011
JP  2011240137 A  12/2011

* cited by examiner

*Primary Examiner* — Vi X Nguyen
(74) *Attorney, Agent, or Firm* — Scully, Scott, Murphy & Presser, P.C.

(57) ABSTRACT

Provided is a digestive-tract treatment method including: pulling, inside a digestive tract (A), an end portion of a first wall portion (A1) positioned at a rim of a treatment target site (B), and moving the first wall portion (A1) to a position on a second wall portion (A2) on an opposite side of the treatment target site (B) from the first wall portion (A1); and joining the first wall portion (A1) and the second wall portion (A2) in a state in which the first wall portion (A1) and the second wall portion (A2) are layered.

10 Claims, 15 Drawing Sheets

DIGESTIVE-TRACT TREATMENT METHOD

TECHNICAL FIELD

The present invention relates to a digestive-tract treatment method.

BACKGROUND ART

A diverticulum that occurs in a digestive tract, such as the colon, is generally not treated until diverticulitis has developed. However, once diverticulitis has developed, the patient has stomachache and high fever, and when the situation becomes more serious, pus is produced and the diverticulum ruptures, thus resulting in peritonitis in some cases.

As a diverticulitis treatment method, a method in which the interior of a diverticulum is washed and the diverticulum is closed up after supplying a drug thereto has been disclosed. By closing up the diverticulum, the recurrence of diverticulitis caused by fecal matter that passes through the colon entering the diverticulum is prevented.

As methods for closing up a diverticulum, a method in which the colon inner surface is covered with a sleeve, a method in which, by means of surgery, the diverticulum is tied with an elastic band outside the colon, and a method in which the diverticulum is pulled into the colon interior by means of suction have been disclosed.

CITATION LIST

Patent Literature

{PTL 1} Japanese Unexamined Patent Application, Publication No. 2011-240137

SUMMARY OF INVENTION

An aspect of the present invention is a digestive-tract treatment method including: pulling, inside a digestive tract, an end portion of a first wall portion positioned at a rim of a treatment target site, and moving the first wall portion to a position on a second wall portion on an opposite side of the treatment target site from the first wall portion; and joining the first wall portion and the second wall portion in a state in which the first wall portion and the second wall portion are layered.

DESCRIPTION OF EMBODIMENT

A digestive-tract treatment method according to an embodiment of the present invention will be described below with reference to the drawings.

Figure 1:
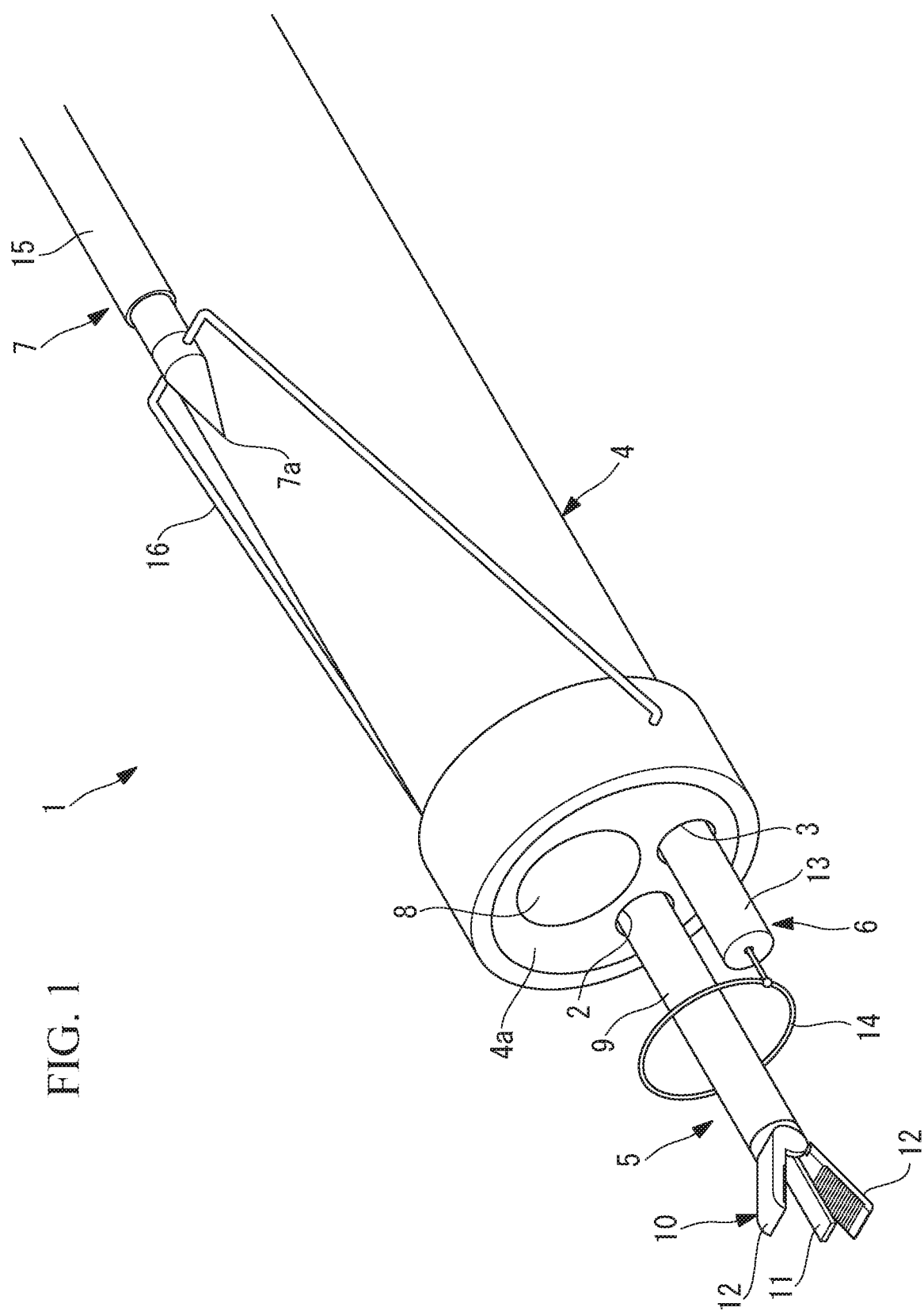
FIG. 1 is a perspective view showing a distal-end portion of a treatment system used in a digestive-tract treatment method according to an embodiment of the present invention.

The digestive-tract treatment method according to this embodiment is a method for treating, for example, a diverticulum (treatment target site, see FIG. 2) B occurring in the colon (digestive tract, see FIG. 2) A. As shown in FIG. 1, a treatment system 1 used in the digestive-tract treatment method according to this embodiment is provided with: an endoscope 4 that is provided with a plurality of channels 2 and 3 passing therethrough in a longitudinal direction; grasping forceps 5 that are made to protrude from a distal-end surface 4a of the endoscope 4 via the first channel 2; a high-frequency snare 6 that is made to protrude from the distal-end surface 4a of the endoscope 4 via the second channel 3; and a suturing device 7 that is attached to the outside of the endoscope 4.

The endoscope 4 is provided with an observation optical system 8 that has a viewing field in front of the distal-end surface 4a.

The grasping forceps 5 are provided with, for example, a grasping portion 10 at a distal end of an elastically deformable shaft 9. The grasping portion 10 is provided with a single stationary jaw 11 and two movable jaws 12 that are independently pivoted with respect to the stationary jaw 11. The grasping forceps 5 are capable of grasping tissue at two locations between the individual movable jaws 12 and the stationary jaw 11.

The high-frequency snare 6 is provided with, at a distal end of an elastically deformable shaft 13, a bipolar electrode 14 formed of a ring-shaped wire, which can tightly bind the tissue, and the high-frequency snare 6 is capable of cutting the tissue by causing a high-frequency current to flow therein in a state in which the tissue inserted inside the ring-shaped wire is tightly bound.

The high-frequency snare 6 is disposed so as to allow the shaft 13 to be moved forward and backward in a longitudinal-axis direction in the second channel 3.

The shaft 9 of the grasping forceps 5 is disposed in a state in which the shaft 9 has passed through the ring-shaped wire that forms the bipolar electrode 14 of the high-frequency snare 6. By moving the high-frequency snare 6 forward in the state in which the tissue is gripped by using the grasping forceps 5, it is possible to easily place the bipolar electrode 14 around the gripped tissue. In this case, for example, the ring-shaped wire serves as an active electrode, and a return electrode is provided in a portion of the shaft 13.

The suturing device 7 is provided with, at a distal end of a shaft 15 possessing elasticity, an apex 7a that can pierce the tissue, and places a tag 17 in the layered tissue in a state in which the apex 7a has pierced therethrough in the layering direction. By doing so, it is possible to hold the layered tissue in a state in which pieces of the tissue are joined with each other.

The suturing device 7 is supported so as to allow the shaft 15 to be moved along the longitudinal axis of the endoscope 4. In addition, a portion in the vicinity of the apex 7a of the suturing device 7 is supported by a distal end of an arm 16 that is attached to a distal-end portion of the endoscope 4 so as to be pivotable about an axis that is orthogonal to the longitudinal axis of the endoscope 4. When the shaft 15 is pushed out forward by an external force applied to a proximal end of the shaft 15, the arm 16 is pivoted, which causes the apex 7a to be moved along an arc-shaped trajectory while causing the shaft 15 to be bent. By doing so, with respect to the tissue that extends, in front of the endoscope 4, in the direction parallel to the longitudinal-axis direction of the endoscope 4, it is possible to pierce the tissue by using the apex 7a in a direction substantially orthogonal to the tissue.

Next, the digestive-tract treatment method according to this embodiment, in which the above-described treatment system 1 is employed, will be described below.

Figure 2:
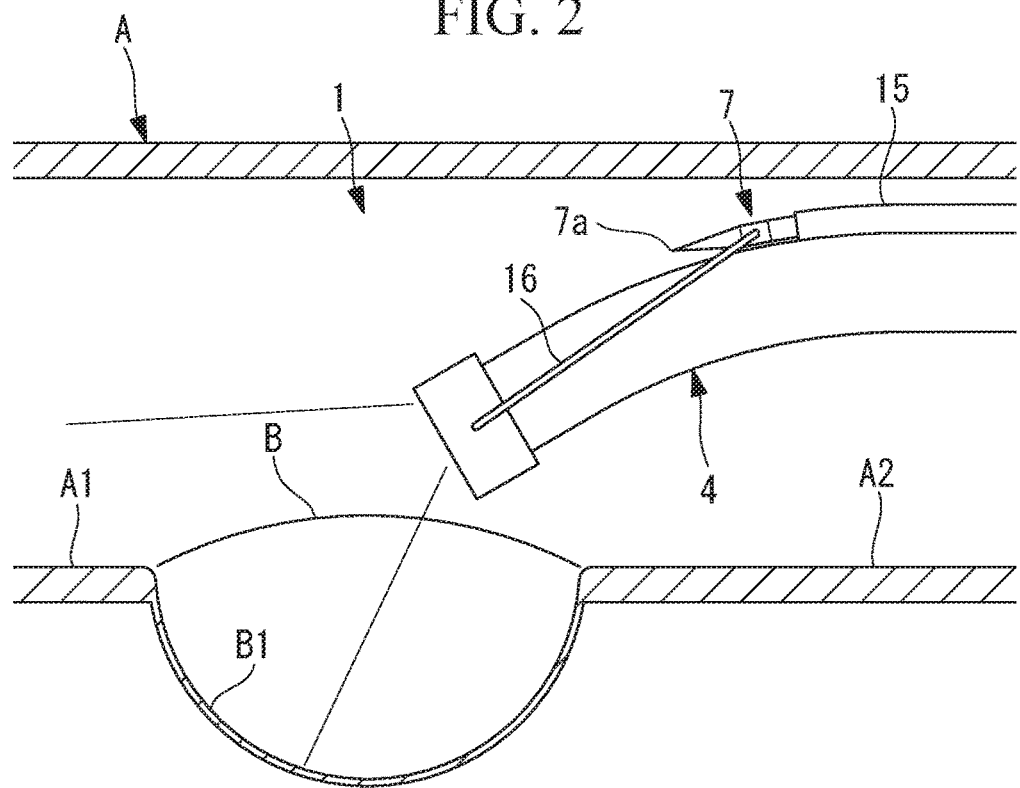
FIG. 2 is a longitudinal cross-sectional view of the colon for explaining an initial observation step in the digestive-tract treatment method according to this embodiment in which the treatment system in FIG. 1 is used.

In the digestive-tract treatment method according to this embodiment, first, as shown in FIG. 2, the endoscope 4 is inserted into the colon A from the anus, and the diverticulum B is placed in the viewing-field area of the observation optical system 8.

Figure 3:
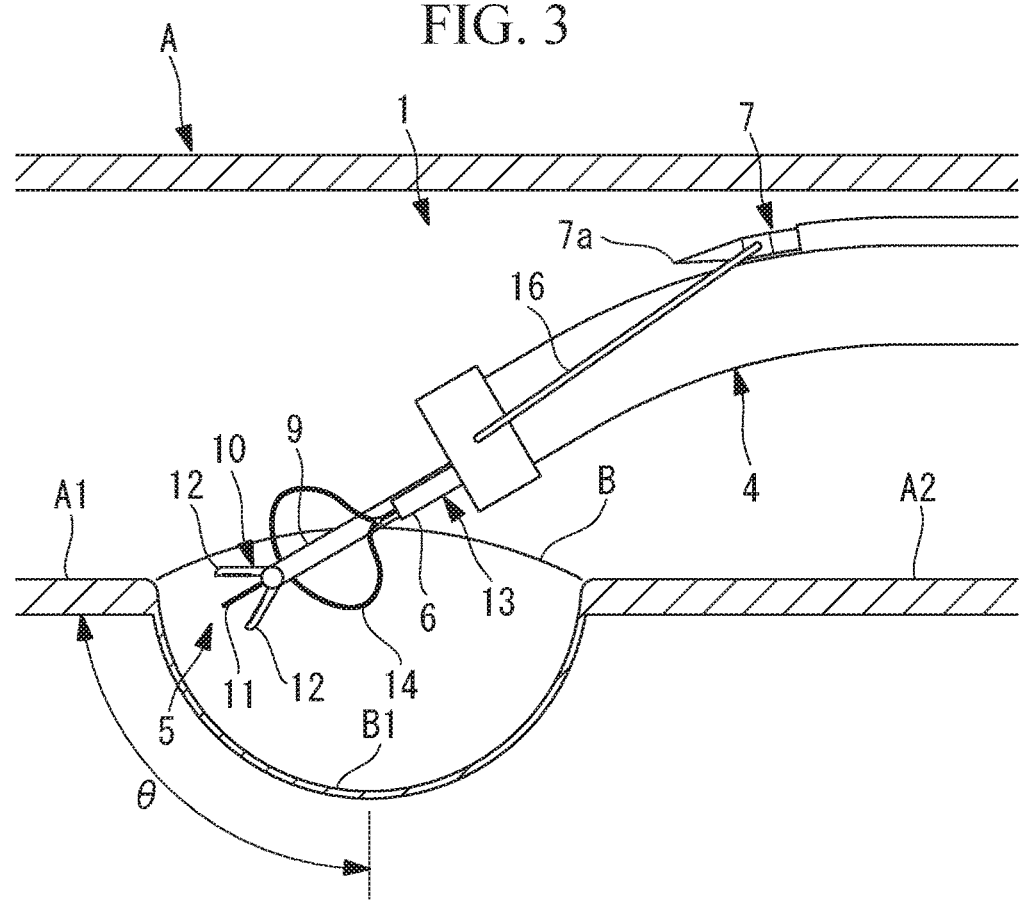
FIG. 3 is a longitudinal cross-sectional view showing a state in which, after the step in FIG. 2, grasping forceps and a high-frequency snare are made to protrude from an endoscope channel.

In this state, the high-frequency snare 6 in the second channel 3 is made to protrude forward from the distal-end surface 4a of the endoscope 4, as shown in FIG. 3. In addition, the grasping forceps 5 in the first channel 2 are made to protrude forward from the distal-end surface 4a of the endoscope 4, and the grasping portion 10 is made to pass through the bipolar electrode 14 of the high-frequency snare 6, which is formed of the ring-shaped wire, from the proximal end side thereof so as to be disposed at a predetermined position farther forward than the bipolar electrode 14 is. This position is a position at which the grasping portion 10 is disposed closer to the proximal end than a position that the apex 7a of the suturing device 7 reaches.

Figure 4:
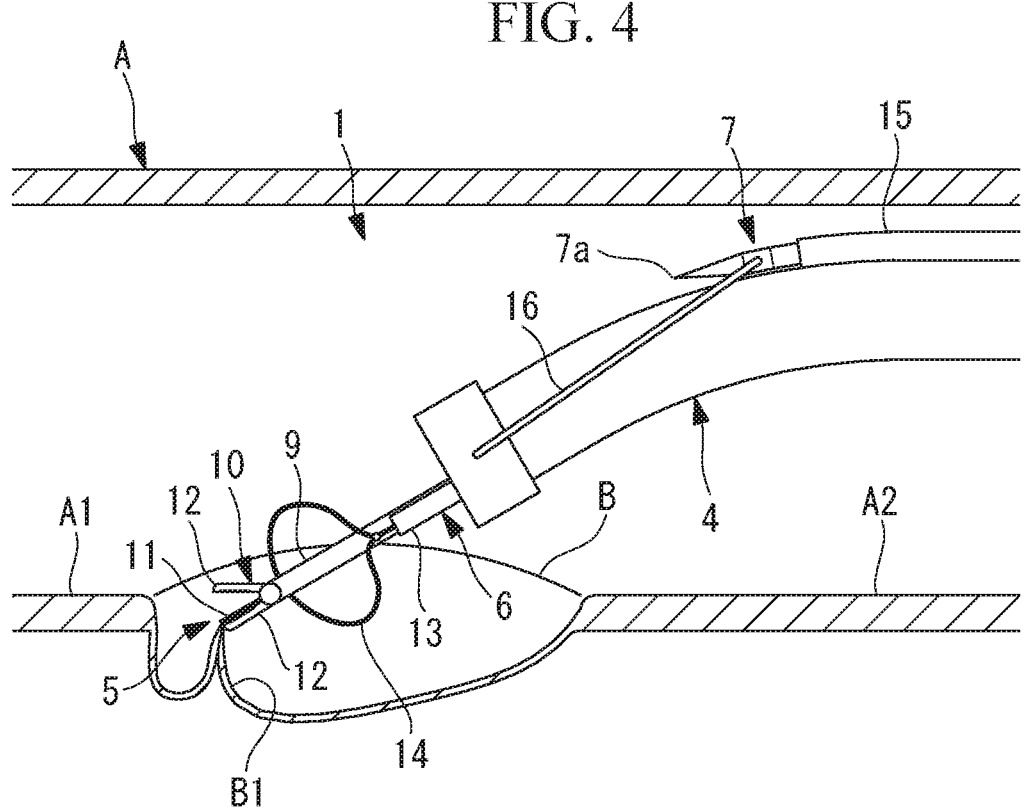
FIG. 4 is a longitudinal cross-sectional view showing a state in which a third wall portion forming a diverticulum is gripped by using the protruded grasping forceps in FIG. 3.

In this state, as shown in FIG. 4, a wall portion (hereinafter referred to as the third wall portion) B1 of the diverticulum B is gripped between one of the movable jaws 12 and the stationary jaw 11 of the grasping portion 10 of the grasping forceps 5 by moving the endoscope 4. The position at which the wall portion B1 of the diverticulum B is gripped is, as indicated by an angle θ in FIG. 3, an arbitrary position between a rim, which is a position on an opposite side of the diverticulum B from the anus, and the deepest position of the diverticulum B.

Figure 5:
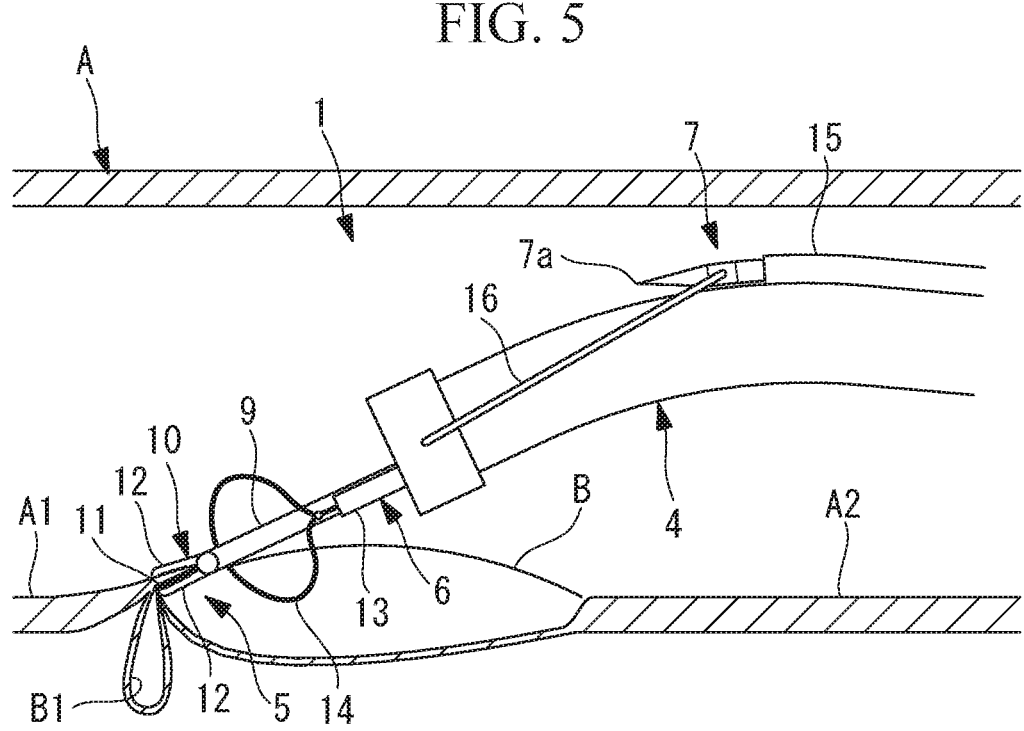
FIG. 5 is a longitudinal cross-sectional view showing a state in which, after the step in FIG. 4, a first wall portion is gripped by using the grasping forceps.

Subsequently, as shown in FIG. 5, a wall portion (hereinafter, referred to as the first wall portion) A1 of the colon A at the rim of the diverticulum B is gripped between the other movable jaw 12 and the stationary jaw 11 of the grasping portion 10 of the grasping forceps 5 by moving the endoscope 4. The position at which the wall portion A1 of the colon A is gripped is, as shown in FIG. 5, an arbitrary position in the vicinity of the rim positioned on the opposite side of the diverticulum B from the anus.

Figure 6:
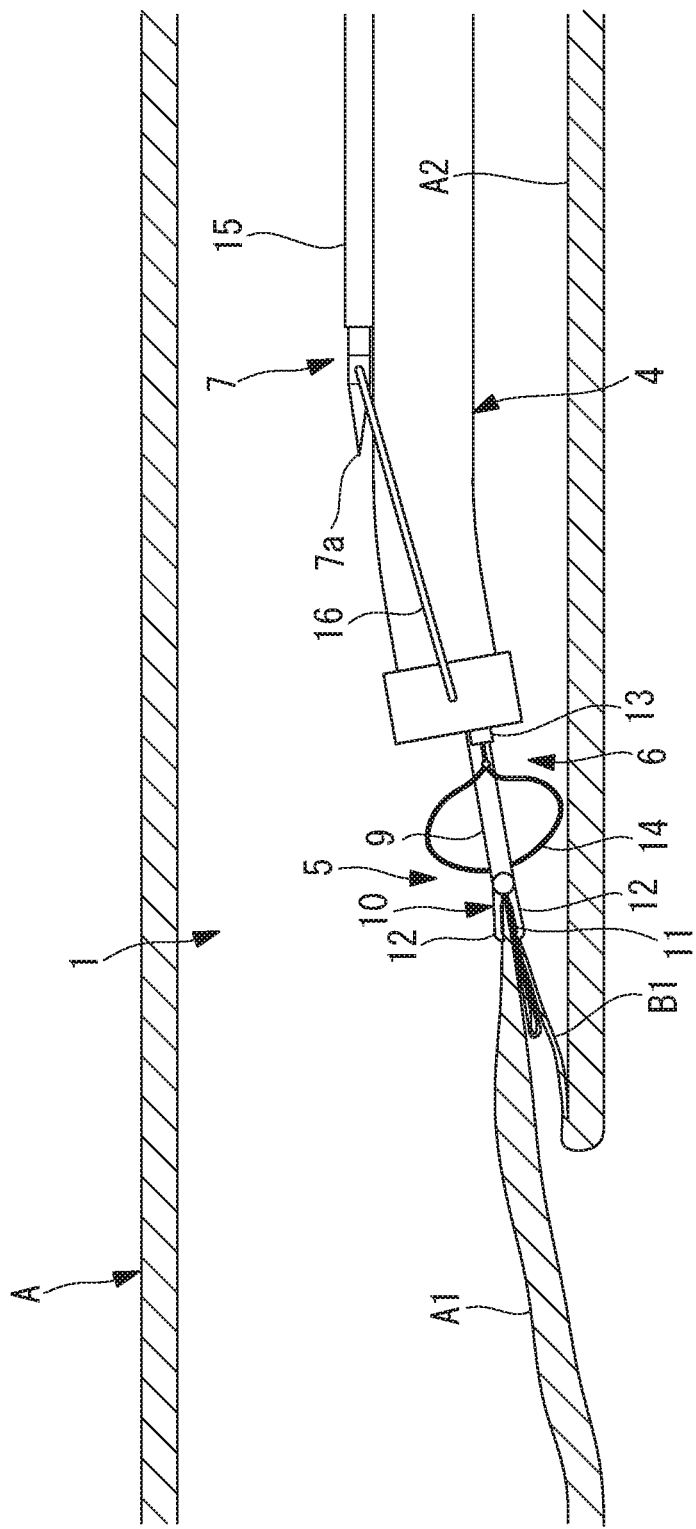
FIG. 6 is a longitudinal cross-sectional view showing a state in which an endoscope is pulled while the first wall portion and the third wall portion continue to be gripped.

Subsequently, as shown in FIG. 6, the endoscope 4 is pulled toward the proximal end. By doing so, the first wall portion A1 and the third wall portion B1 gripped by the grasping portion 10 are pulled toward the anus, and, as shown in FIG. 6, the pulled first wall portion A1 and third wall portion B1 and a wall portion (second wall portion) A2 of the colon A, which is closer to the anus than the diverticulum B is, are arranged in a layered state with the wall portion B1 of the diverticulum B interposed between the first wall portion A1 and the second wall portion A2.

At this time, it is preferable that the endoscope 4 be pulled in a direction in which the first wall portion A1 being gripped by the grasping forceps 5 is oriented along the second wall portion A2.

Figure 7:
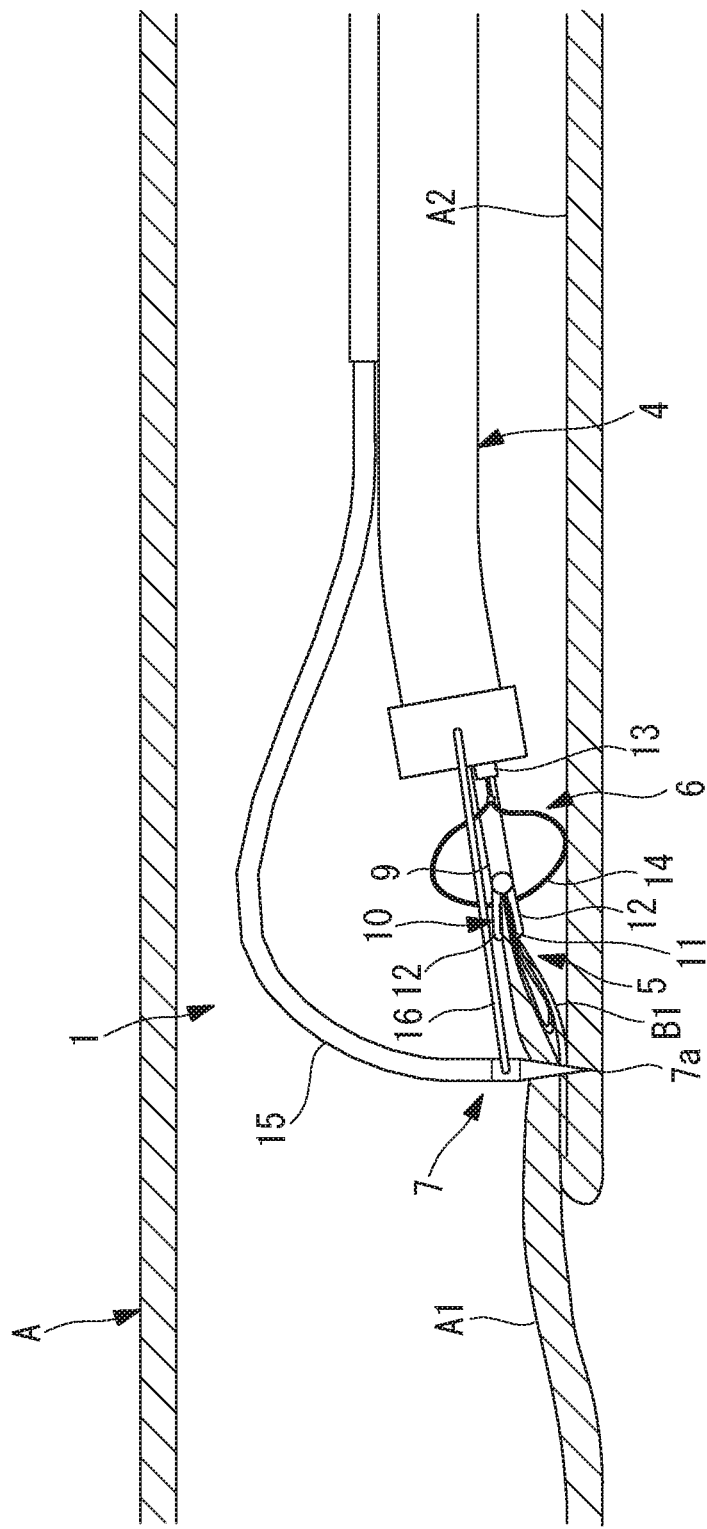
FIG. 7 is a longitudinal cross-sectional view for explaining a step for suturing, after the step in FIG. 6, the layered first, second, and third wall portions.
Figure 8:
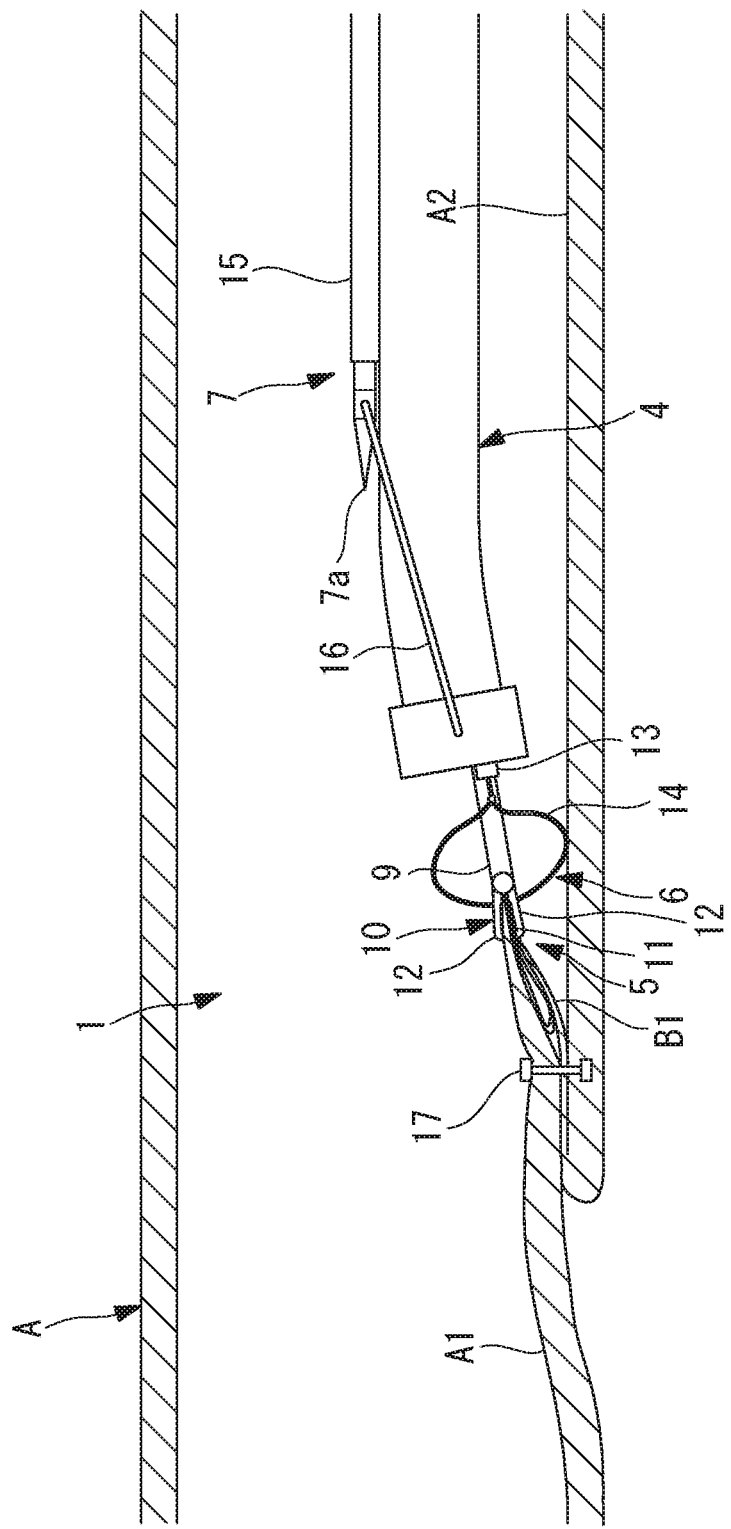
FIG. 8 is a longitudinal cross-sectional view showing a state in which suturing has been completed by means of the step in FIG. 7.

Next, as shown in FIG. 7, the arm 16 is pivoted by moving the shaft 15 of the suturing device 7 forward, the apex 7a is moved in an arc shape while bending the shaft 15, and the three layered wall portions A1, A2, and B1 are pierced with the apex 7a in the layering direction. At this time, the apex 7a passes through the first wall portion A1 and the third wall portion B1, and pierces them until reaching a muscular-layer position of the second wall portion A2. Then, a tag 17 carried inside the suturing device 7 is placed at this position, and, subsequently, the suturing device 7 is retracted. By doing so, as shown in FIG. 8, the three wall portions A1, A2, and B1 are sutured in the layered state by means of the tag 17.

Figure 9:
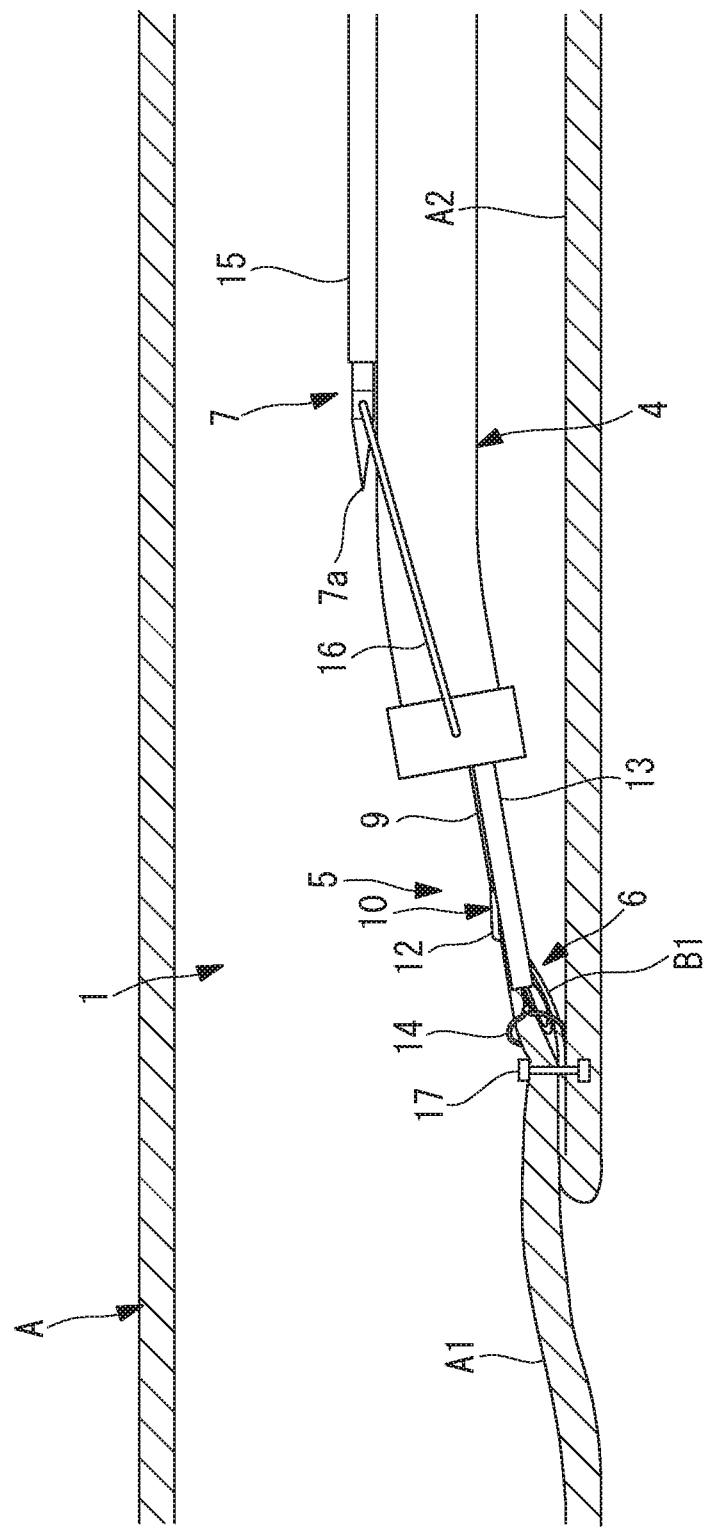
FIG. 9 is a longitudinal cross-sectional view showing a state in which, from the state in FIG. 8, the high-frequency snare is moved forward and tightly bound.

Subsequently, as shown in FIG. 9, by moving the shaft 13 of the high-frequency snare 6 forward, the tissue being gripped by the grasping forceps 5 is made to pass through the ring-shaped wire, which is the bipolar electrode 14. By doing so, the wire is wound around the tissue. Thus, a state in which the wire is wound around the tissue between the position gripped by the grasping forceps 5 and the position at which suturing is performed by using the suturing device 7 is established, and the tissue is cut by causing a high-frequency current to flow in the wire.

Figure 10:
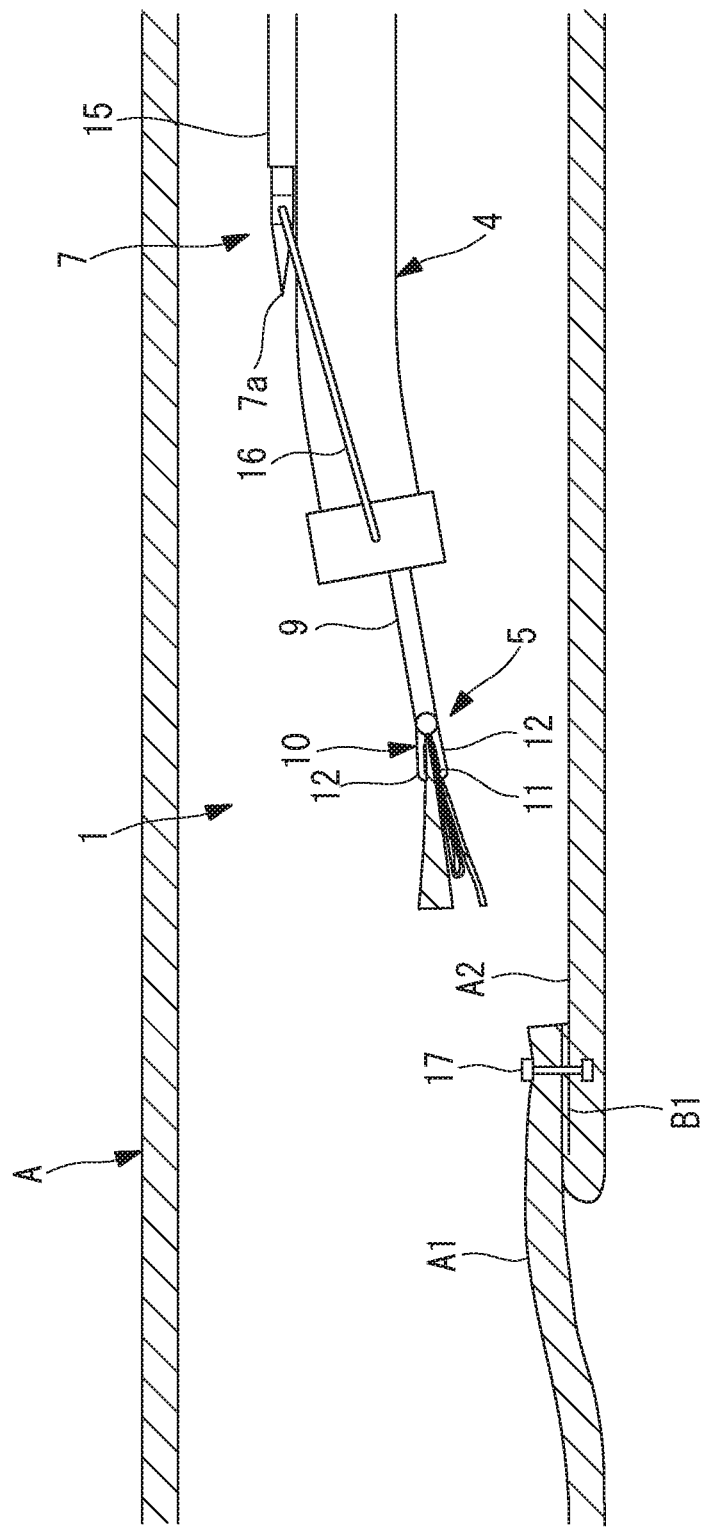
FIG. 10 is a longitudinal cross-sectional view showing a state in which tissue is excised by causing a high-frequency current to flow in the high-frequency snare that has been tightly bound in the step in FIG. 9.

As shown in FIG. 10, the cut tissue is recovered outside the body by pulling out the endoscope 4 from the colon A in a state in which the tissue is gripped by using the grasping forceps 5.

In this case, unlike covering an inner surface of the colon A with a sleeve, as in the related art, because the diverticulum B is closed off by using the wall surface of the colon A itself, there is an advantage in that there is no troublesomeness associated with positioning, etc. with respect to the position at which the diverticulum B is covered. In addition, unlike tying, by means of surgery, the diverticulum B by using an elastic band outside the colon A, as in the related art, there is an advantage in that it is possible to perform treatment less invasively by using the endoscope 4. Furthermore, it is possible to prevent the recurrence of a situation in which, for example, the diverticulum B that has been pulled inward protrudes outward again due to the internal pressure in the colon A.

In addition, in this embodiment, because the end portion of the first wall portion A1 of the colon A, which is on the opposite side of the diverticulum B from the anus, is pulled toward the anus and is sutured to the second wall portion A2 of the colon A that is closer to the anus than the diverticulum B is, as shown in FIG. 10, it is possible to orient a gap between the first wall portion A1 and the second wall portion A2 and a cut surface thereat so as to face toward the anus. In other words, it is possible to orient the gap between the first wall portion A1 and the second wall portion A2 and the cut surface thereat toward the downstream side with respect to the direction in which fecal matter flows due to peristalsis. By doing so, because fecal matter is less likely to enter the diverticulum B, it is possible to prevent the recurrence of diverticulitis, and it is possible to reduce the risk of inflammation occurring in the tissue.

In addition, because the first wall portion A1, the third wall portion B1, and the second wall portion A2 are sutured in the layered state, the pressure in the colon A acts in the layering direction. In other words, the pressure in the colon A acts in a direction in which the individual wall portions A1, A2, and B1 are brought into tight contact with each other, and the pressure does not act in the direction in which the suture would be removed; therefore, there is an advantage in that it is possible to maintain a sound joined state for an extended period of time.

In addition, with this embodiment, through the operation of grasping the first wall portion A1 after grasping the third wall portion B1 by using the two movable jaws 12, the grasping forceps 5 gather a portion of the diverticulum B toward the first wall portion A1, and thus, the grasping forceps 5 can pull the remaining diverticulum B in a compact state. By doing so, there is an advantage in that it is possible to suture the diverticulum B between the first wall portion A1 and the second wall portion A2 in a state in which slack in the diverticulum B is quickly eliminated by reducing the amount by which the endoscope 4 is moved until the entire diverticulum B is arranged along the second wall portion A2, in other words, until reaching the position on the second wall portion A2 on the opposite side from the first wall portion A1.

In addition, with this embodiment, when pulling the first wall portion A1 toward the anus, because the first wall portion A1 is moved until reaching the position on the second wall portion A2 on the opposite side from the first wall portion A1, there is an advantage in that, even if blood vessels or other organs are present outside the diverticulum B, it is possible to prevent the blood vessels or other organs from being wrapped up with the third wall portion B1 that is pulled into the colon A.

Note that, although this embodiment has been described in terms of an example of a case in which the grasping forceps 5 have the grasping portion 10 that can grip tissue at two locations, alternatively, grasping forceps 5 that have a grasping portion 10 that can grip tissue only at one location may be employed. In this case, because only the first wall portion A1 is gripped and pulled by using the grasping forceps 5, in the case in which the entire third wall portion B1 that forms the diverticulum B is interposed between the first wall portion A1 and the second wall portion A2, it is necessary to increase the amount by which the endoscope 4 is pulled.

On the other hand, because, in the state in which diverticulitis is not occurring, it suffices to close up an opening of the diverticulum B leading into the interior of the colon A even in a state in which a portion of the third wall portion B1 is slack outside the colon A, the pulled amount may be set at a minimum amount that is required to allow the first wall portion A1 and the second wall portion A2 to be sutured. In the case in which diverticulitis is not occurring, the step of performing excision by means of the high-frequency snare 6 may be omitted.

Figure 11:
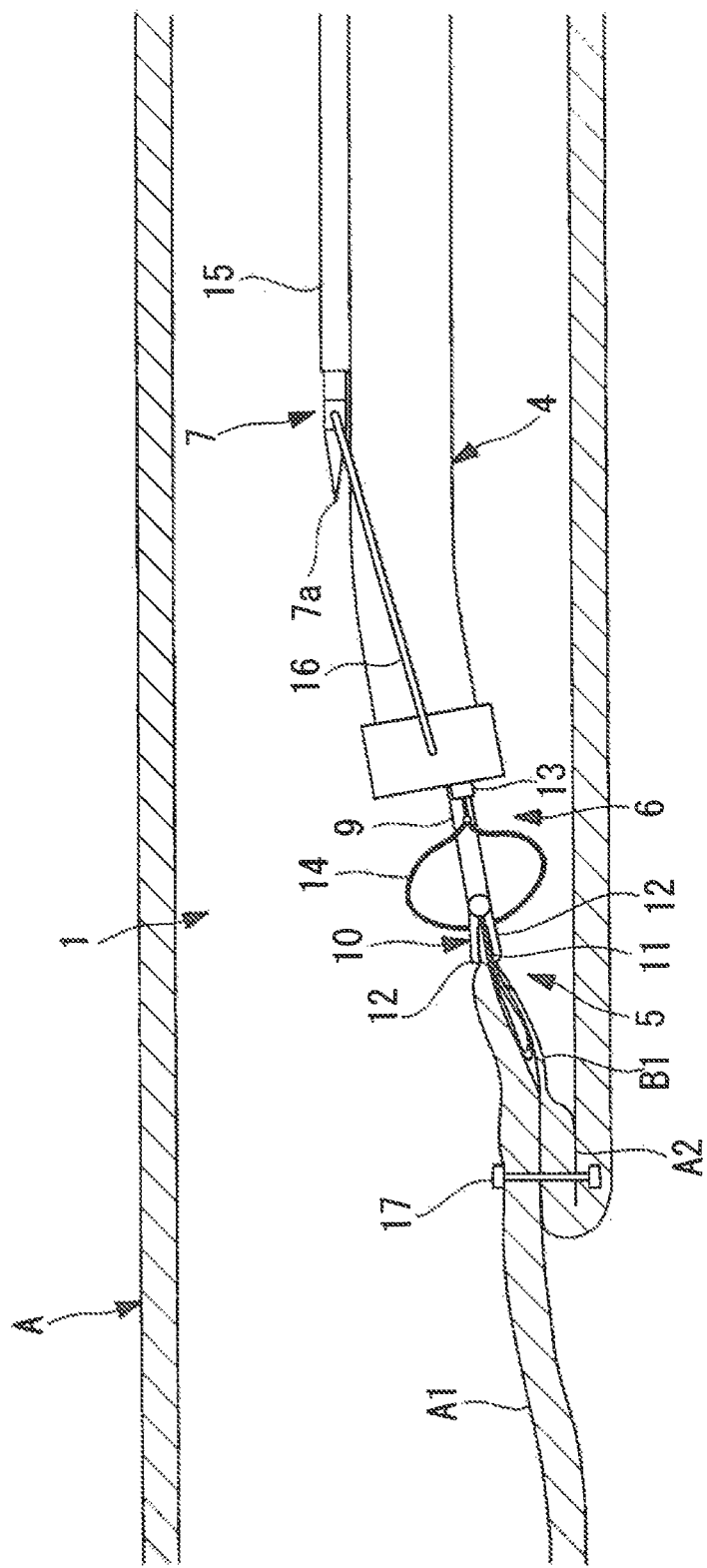
FIG. 11 is a longitudinal cross-sectional view showing a modification of the state in FIG. 8.
Figure 12:
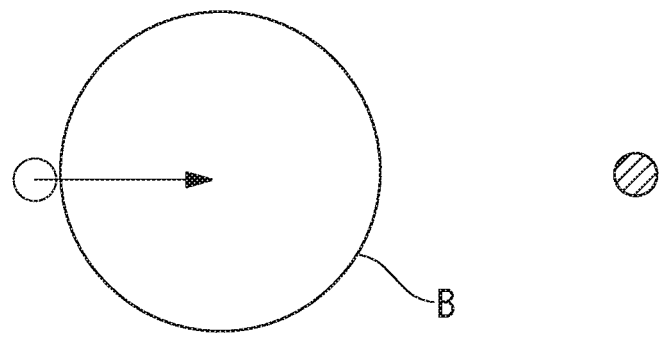
FIG. 12 is a front view of the diverticulum for explaining the grasping position of the first wall portion and a marking provided on the second wall portion.
Figure 13:
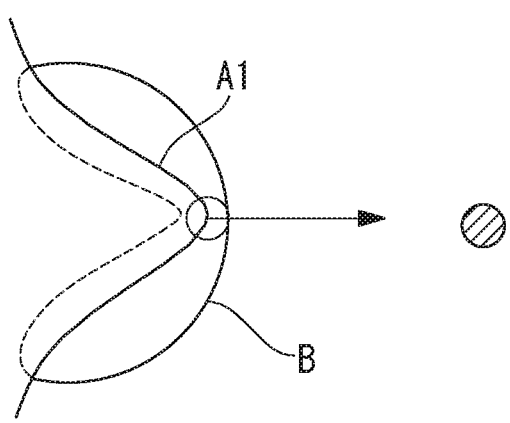
FIG. 13 is a front view showing a state in which the first wall portion being gripped in FIG. 12 is in the process of being pulled.
Figure 14:
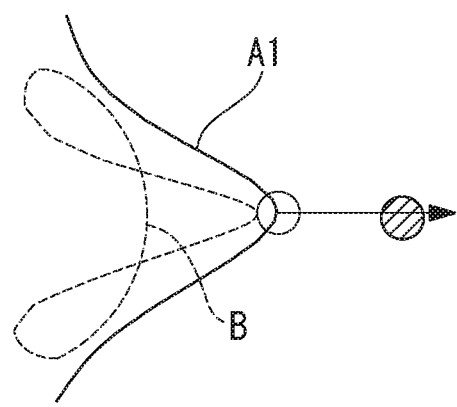
FIG. 14 is a front view showing a state in which further pulling is performed from the state in FIG. 13, and thus, the diverticulum is hidden.

In addition, in the case in which diverticulitis is occurring in the entire diverticulum, there are cases in which it is necessary to remove the entire third wall portion B1 forming the diverticulum B. In this case, the first wall portion A1 may be pulled until the second wall portion A2 is folded back by further increasing the amount by which the endoscope 4 is pulled in the state in which the first wall portion A1 is gripped by using the grasping forceps 5. Thus, as shown in FIG. 11, instead of the layered state of each wall portions shown in FIG. 8, it is possible to excise the entire diverticulum B by suturing the second wall portion A2, which has formed two layers by being folded back, and the first wall portion A1, and by cutting the first wall portion A1 and one of the layers of the second wall portion A2. The other procedural steps are the same as those in the above embodiment.

In addition, when the first wall portion A1 is pulled toward the anus, as shown in FIGS. 12 to 15, with an increase in the pulled amount, the pulled first wall portion A1 makes it impossible to visually check the diverticulum B. At positions in FIGS. 14 and 15, it is entirely impossible to visually check the entire diverticulum B. Because of this, it is difficult to determine whether or not the first wall portion A1 has sufficiently been pulled until the position to be pierced by using the apex 7a of the suturing device 7 does not reach the diverticulum B. Therefore, as indicated by hatching in FIGS. 12 to 15, it is preferable that a mark be provided by using dye, cautery by means of a high-frequency knife, or the like on a surface of the second wall portion A2 separated from the diverticulum B farther toward the anus by a predetermined distance.

Figure 15:
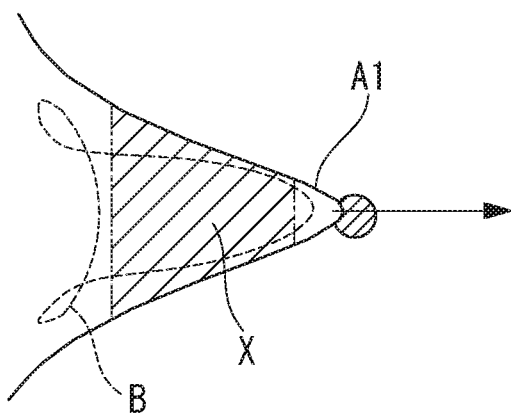
FIG. 15 is a front view showing a state in which further pulling is performed from the state in FIG. 14, and thus, the first wall portion is pulled until reaching the marking.

In other words, as shown in FIG. 15, by pulling the first wall portion A1 which is gripped by the grasping forceps 5 until reaching the position at which the first wall portion A1 reaches the mark, it is possible to reliably perform suturing, by using the suturing device 7, at the position at which the first wall portion A1 and the second wall portion A2 are layered (area indicated by diagonal lines X in FIG. 15).

Figure 16:
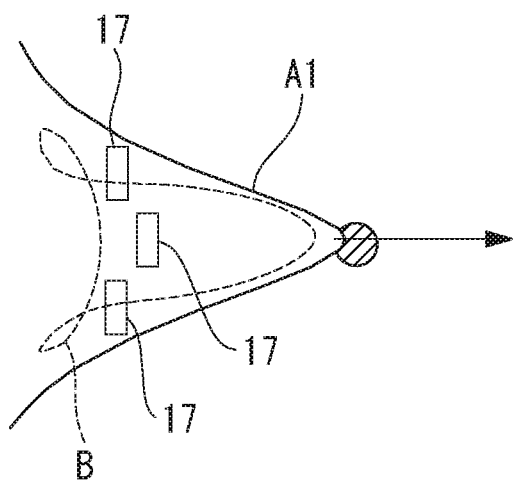
FIG. 16 is a front view showing a state in which the first wall portion and second wall portion in FIG. 15 are sutured.
Figure 17:
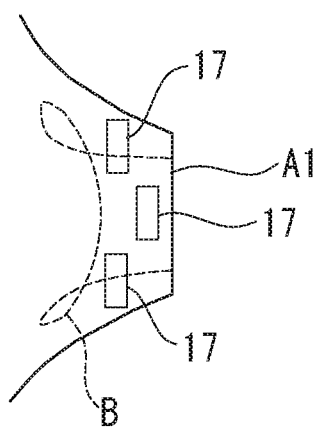
FIG. 17 is a front view showing a state in which tissue is excised after FIG. 16.

In addition, suturing performed by using the suturing device 7 may be performed at multiple locations, as shown in FIG. 16. In this case, cutting by means of the high-frequency snare 6 may be performed after performing suturing by using the final tag 17, as shown in FIG. 17.

In addition, in this embodiment, although the colon A has been described as an example of the digestive tract and the diverticulum B has been described as an example of the treatment target site, there is no limitation thereto, and the present invention may be applied to other arbitrary digestive tracts, for example, the small intestine, the duodenum, etc. In addition, the treatment target site is not limited to the diverticulum B, and the present invention may be applied to a lesion, such as a tumor or the like, occurring in the inner surface of the digestive tract.

Figure 18A:
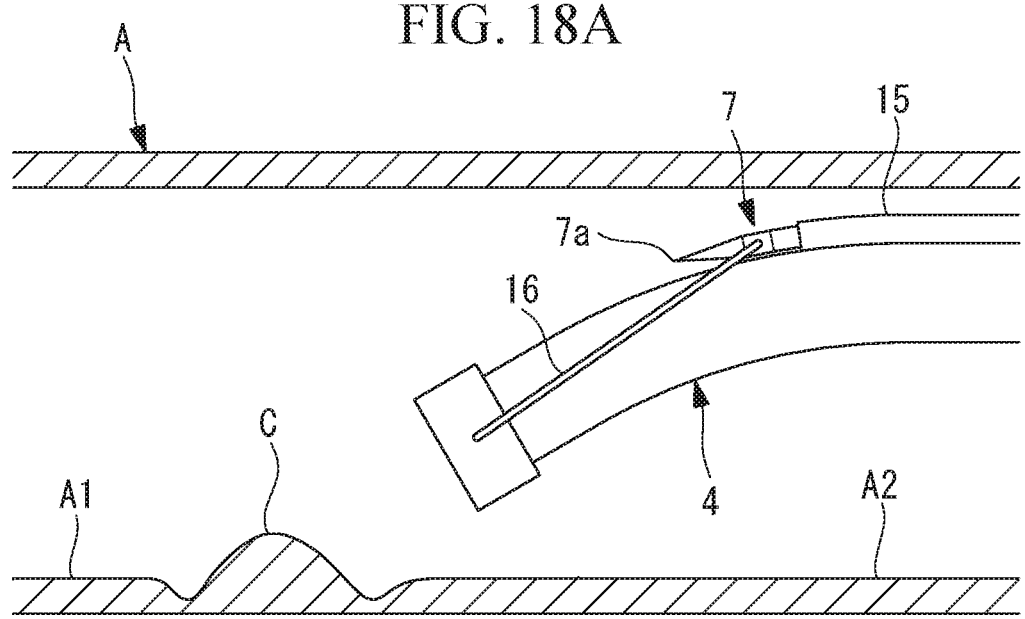
FIG. 18A is a longitudinal cross-sectional view showing a modification of the state in FIG. 2.

In this case also, as with the case of excising the entire diverticulum B, described above, first the endoscope 4 is inserted into the colon A from the anus, and a tumor (treatment target site) C is placed in the viewing-field area of the observation optical system 8, as shown in FIG. 18A.

Figure 18B:
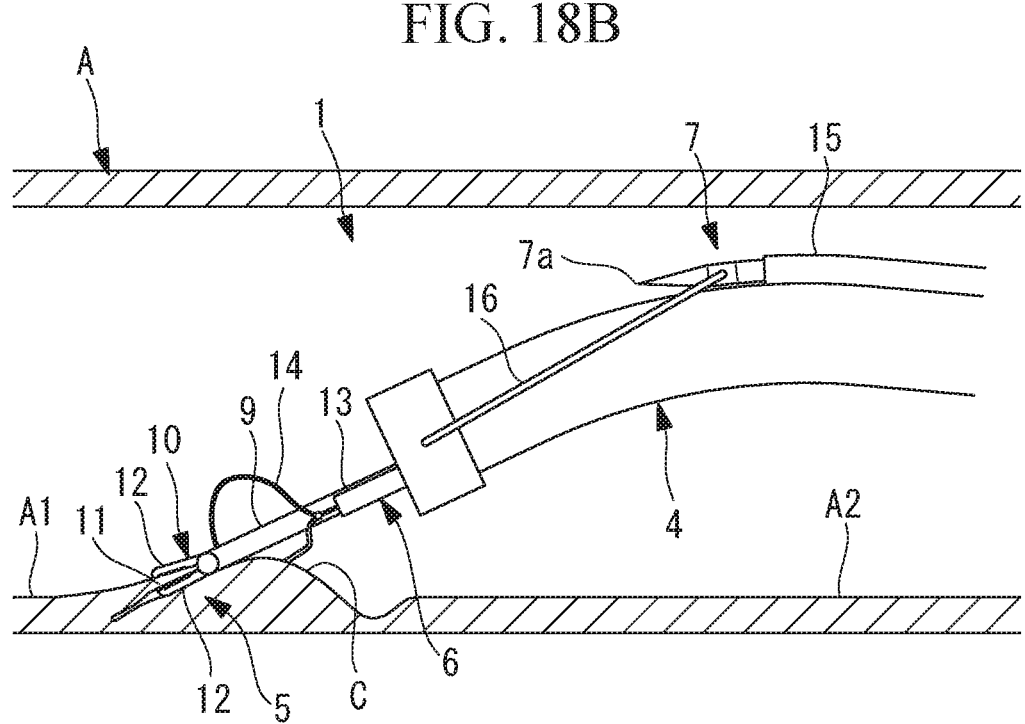
FIG. 18B is a longitudinal cross-sectional view showing a state in which, after the step in FIG. 18A, the first wall portion is gripped by using the grasping forceps.

In this state, as shown in FIG. 18B, the first wall portion A1 is gripped between one of the movable jaws 12 and the stationary jaw 11 of the grasping portion 10 of the grasping forceps 5 by moving the endoscope 4.

Figure 18C:
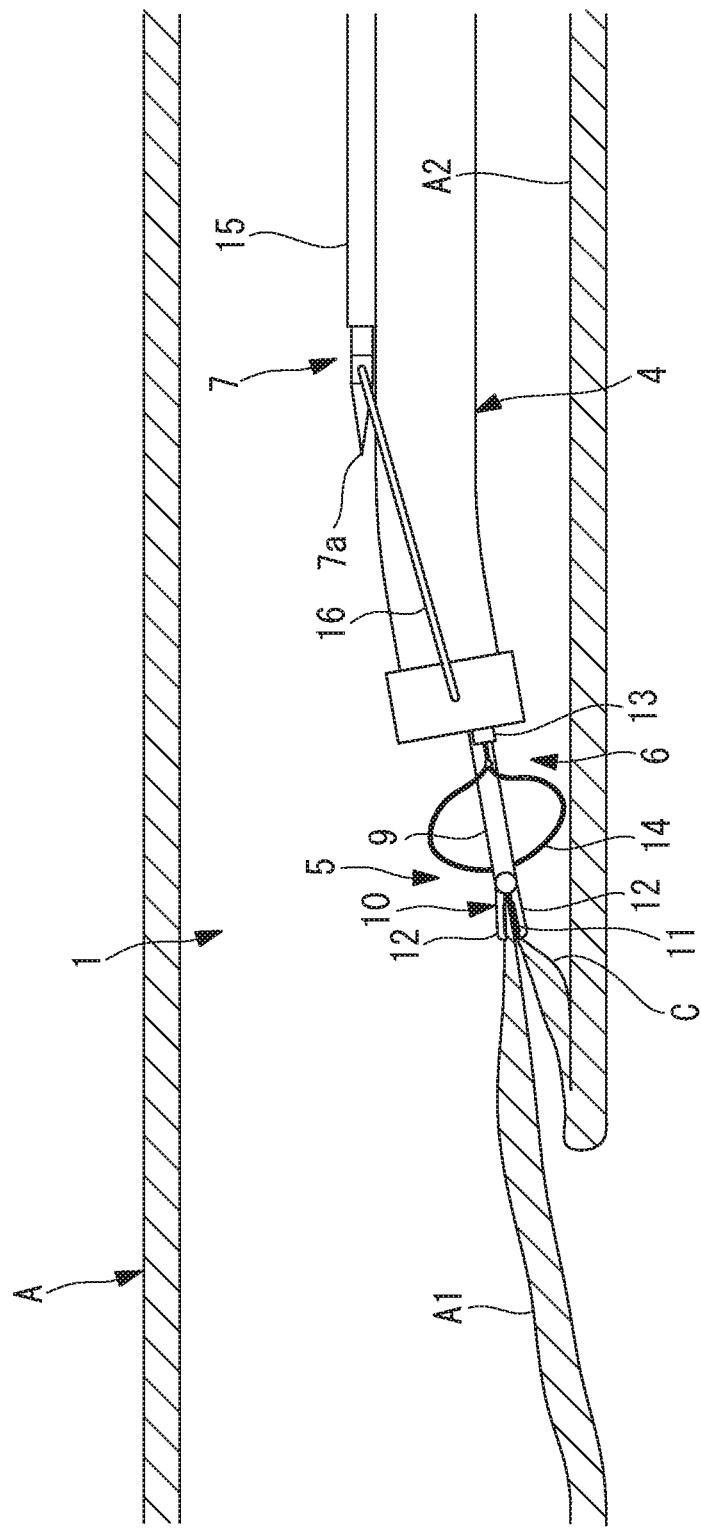
FIG. 18C is a longitudinal cross-sectional view showing a state in which, after the step in FIG. 18B, the endoscope is pulled while the first wall portion continues to be gripped.

Subsequently, as shown in FIG. 18C, the endoscope 4 is pulled toward the proximal end, and the pulled first wall portion A1 and the second wall portion A2 of the colon A, which is closer to the anus than the tumor C is, are arranged in a layered state with the tumor C interposed therebetween.

Figure 18D:
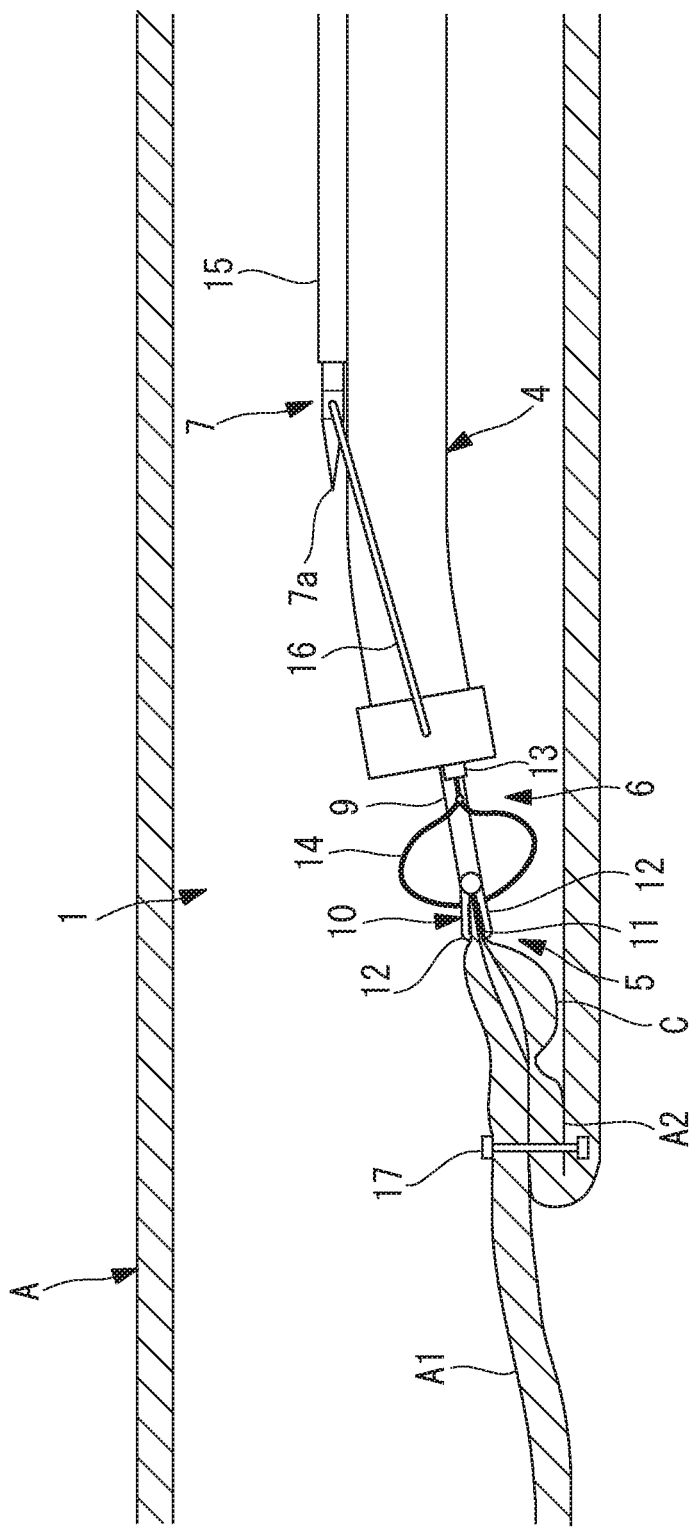
FIG. 18D is a longitudinal cross-sectional view showing a state in which suturing is performed after the step in FIG. 18C.

Next, as shown in FIG. 18D, the arm 16 is pivoted by moving the shaft 15 of the suturing device 7 forward, the apex 7a is moved in an arc shape while bending the shaft 15, and the two layered wall portions A1 and A2 and tumor C are pierced with the apex 7a in the layering direction.

Figure 18E:
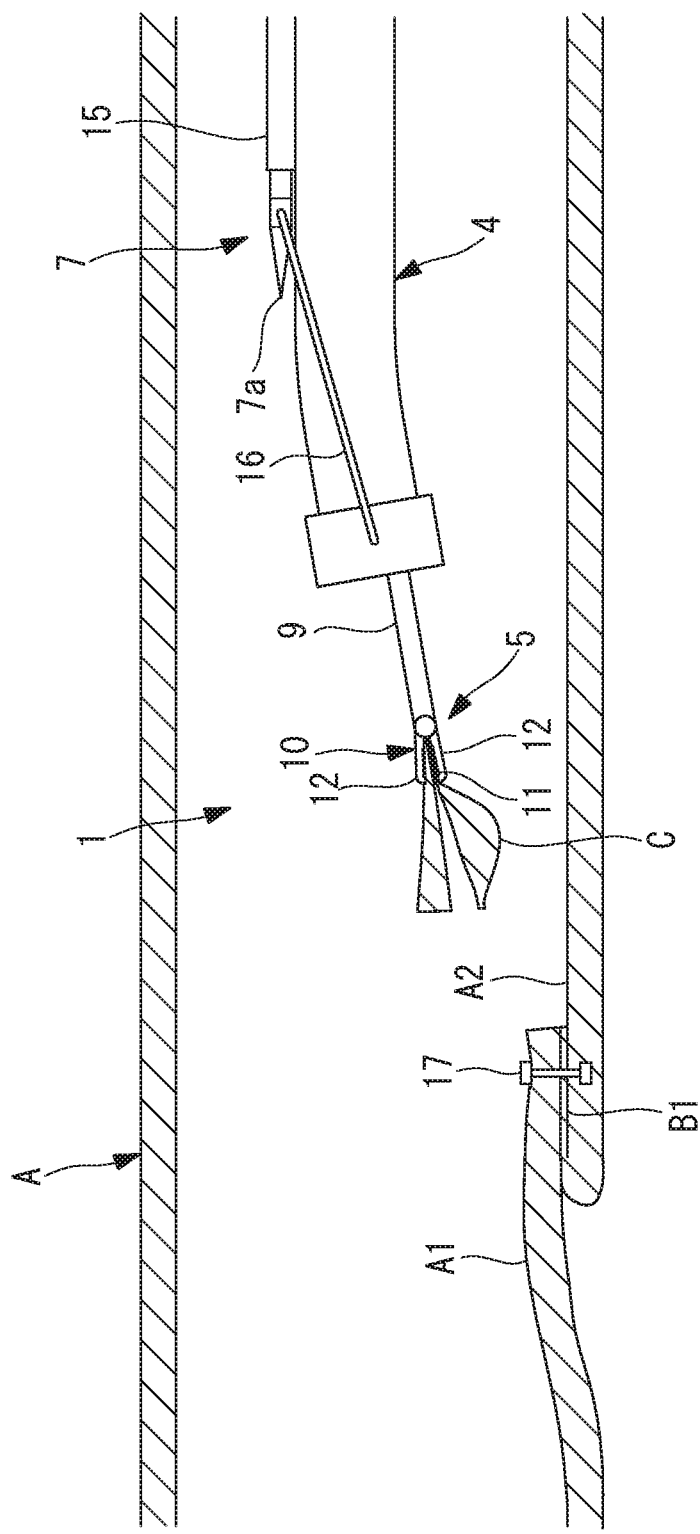
FIG. 18E is a longitudinal cross-sectional view showing a state in which the tissue is excised after the step in FIG. 18D.

Subsequently, the wire is wound around the tissue. Thus, as shown in FIG. 18E, in the state in which the wire is wound around the tissue between the position gripped by using the grasping forceps 5 and the position at which suturing is performed by using the suturing device 7, it is possible to excise the entire lesion, such as the tumor C or the like, by causing a high-frequency current to flow in the wire.

In addition, in this embodiment, although the ring-shaped wire is employed as the bipolar electrode 14 so as to serve as the high-frequency snare 6, alternatively, the ring-shaped wire of the high-frequency snare 6 may be a monopolar electrode.

In addition, although this embodiment has been described in terms of an example in which tissue is gripped by using the grasping forceps 5, alternatively, a form in which tissue is pulled by means of endoscopic suction may be employed.

In addition, an aspect of the present invention is a digestive-tract treatment method including: pulling, inside a digestive tract, a first wall portion positioned at a rim of a treatment target site, and moving the first wall portion to a position at which the first wall portion is placed along a second wall portion on an opposite side of the treatment target site from the first wall portion; and joining the first wall portion and the second wall portion in a layered state.

With this aspect, it is possible to achieve a state in which the treatment target site is covered with the first wall portion by moving the first wall portion to the position at which the first wall portion is placed along the second wall portion by pulling the first wall portion of the treatment target site. By joining, in this state, the first wall portion and the second wall portion in the layered state, it is possible to achieve a state in which the treatment target site is covered so as not to be exposed inside the digestive tract. By doing so, it is possible to prevent fecal matter flowing in the digestive tract from coming into contact with the treatment target site.

In the above-described aspect, the first wall portion may be positioned on an opposite side of the treatment target site from the anus, and the second wall portion may be positioned closer to the anus than the treatment target site is.

With this configuration, in the state in which the first wall portion and the second wall portion are joined in the layered state, it is possible to orient the joining surfaces between the first wall portion and the second wall portion toward the anus, in other words, toward the downstream side with respect to the flow of the fecal matter. By doing so, the chance of the fecal matter flowing in the digestive tract getting in between the joining surfaces is reduced, and thus, it is possible to prevent the occurrence of inflammation therein.

In addition, in the above-described aspect, by pulling both the first wall portion and a third wall portion, which forms the treatment target site, the first wall portion may be moved to a position at which the first wall portion is placed along the second wall portion.

With this configuration, in the case in which the third wall portion is slack, it is possible to pull the wall portions together, and thus, it is possible to reduce the final amount of movement thereof.

In addition, in the above-described aspect, after joining the first wall portion and the second wall portion, at least a portion of the first wall portion and the third wall portion is cut between the position at which the first wall portion is pulled and the joining position.

With this configuration, by excising an extra protrusion formed as a result of layering the first wall portion and the second wall portion, it is possible to prevent the extra protrusion from remaining in the digestive tract.

In addition, in the above-described aspect, the first wall portion and the second wall portion may be joined by means of suturing.

With this configuration, it is possible to join the first wall portion and the second wall portion in a simple manner.

In addition, in the above-described aspect, the digestive tract may be the colon, and the treatment target site may be a diverticulum.

With this configuration, by closing up the diverticulum and by removing a portion or the entirety thereof, it is possible to prevent the occurrence and recurrence of diverticulitis.

In addition, in the above-described aspect, the first wall portion and the second wall portion may be joined with the third wall portion interposed therebetween.

With this configuration, in the case in which diverticulitis is not occurring, it is possible to perform treatment by suppressing the amount by which the first wall portion is moved.

In addition, in the above-described aspect, the entire third wall portion may be excised after pulling the first wall portion until the second wall portion is folded back and joining the second wall portion, which has formed two layers by being folded back, and the first wall portion in the layered state.

With this configuration, in the case in which it is not desirable to leave a remnant treatment target site, it is possible to excise, in a simple manner, the entire third wall portion forming the treatment target site.

REFERENCE SIGNS LIST

A colon (digestive tract)
A1 wall portion (first wall portion)
A2 second wall portion B diverticulum (treatment target site)
B1 wall portion (third wall portion)
C tumor (treatment target site)

The invention claimed is:

1. A digestive-tract treatment method comprising:
   pulling, inside a digestive tract, an end portion of a first wall portion positioned at a rim of a treatment target site and a third wall portion, which forms the treatment target site, and moving the first wall portion to a position on a second wall portion on an opposite side of the treatment target site from the first wall portion such that the first wall portion is placed along the second wall portion, the first wall portion being positioned on an opposite side of the treatment target site from the anus, the second wall portion being positioned closer to the anus than the treatment target site;
   joining the first wall portion and the second wall portion in a state in which the first wall portion and the second wall portion are layered, and
   subsequent to the joining, cutting at least a portion of the first wall portion and the third wall portion between a position at which the first wall portion and the second wall portion are joined and the end portion of the first wall portion.

2. The digestive-tract treatment method according to claim 1,
   wherein pulling comprises pulling the first wall portion until the second wall portion is folded back,
   the joining comprises joining the second wall portion and the first wall portion in a state in which the second wall portion, which has formed two layers by being folded back, and the first wall portion are layered, and
   the cutting comprises excising the entire third wall portion.

3. The digestive-tract treatment method according to claim 1, wherein the joining comprises suturing the first wall portion and the second wall portion.

4. The digestive-tract treatment method according claim 1,
   wherein the digestive tract is the colon, and
   the treatment target site is a diverticulum.

5. The digestive-tract treatment method according to claim 4, wherein the first wall portion and the second wall portion are joined with a portion of the diverticulum interposed therebetween.

6. A treatment method of a colon, the method comprising:
   grabbing a first wall portion of the colon at a first position relative to a rim around a treatment target site;
   pulling the first wall portion beyond a second wall portion of the colon in a direction of an anus, the second wall portion being at a second position relative to the rim around the treatment target site, the second position being closer to the anus than the first position;
   moving the first wall portion in the direction of the anus until the treatment target site is closer to the anus than the second position; and
   subsequent to the moving, joining the first wall portion and the second wall portion in a state in which the first wall portion and the second wall portion are layered.

7. The treatment method according to claim 6, wherein the first position is at the rim.

8. The treatment method according to claim 6, wherein the second position is at the rim.

9. A digestive-tract treatment method comprising:
   pulling, inside a digestive tract, an end portion of a first wall portion positioned at a rim of a treatment target site, and moving the first wall portion to a position on a second wall portion on an opposite side of the treatment target site from the first wall portion;
   joining the first wall portion and the second wall portion in a state in which the first wall portion and the second wall portion are layered; and
   subsequent to the joining, cutting at least a portion of the first wall portion and a portion between the first wall portion and a third wall portion, which forms the treatment target site, between a position at which the first wall portion and the second wall portion are joined and the end portion of the first wall portion.

10. The digestive-tract treatment method according to claim 9,
    wherein the digestive tract is the colon,
    the treatment target site is a tumor, and
    wherein the pulling comprises pulling the first wall portion until the second wall portion is folded back,
    the joining comprises joining the second wall portion and the first wall portion in a state in which the second wall portion, which has formed two layers by being folded back, and the first wall portion are layered, and
    the cutting comprises excising the tumor from the colon.

* * * * *